United States Patent
Kim et al.

(10) Patent No.: US 12,129,491 B2
(45) Date of Patent: Oct. 29, 2024

(54) METHODS AND COMPOSITIONS RELATING TO LUNG CELL DIFFERENTIATION

(71) Applicant: CHILDREN'S MEDICAL CENTER CORPORATION, Boston, MA (US)

(72) Inventors: Carla F. Kim, Boston, MA (US); Samuel P. Rowbotham, Brookline, MA (US); Joo-Hyeon Lee, Cheshire (GB)

(73) Assignee: CHILDREN'S MEDICAL CENTER CORPORATION, Boston, MA (US)

( * ) Notice: Subject to any disclaimer, the term of this patent is extended or adjusted under 35 U.S.C. 154(b) by 806 days.

(21) Appl. No.: 16/097,643

(22) PCT Filed: Jun. 8, 2017

(86) PCT No.: PCT/US2017/036530
§ 371 (c)(1),
(2) Date: Oct. 30, 2018

(87) PCT Pub. No.: WO2017/218287
PCT Pub. Date: Dec. 21, 2017

(65) Prior Publication Data
US 2019/0136199 A1    May 9, 2019

Related U.S. Application Data

(60) Provisional application No. 62/350,237, filed on Jun. 15, 2016.

(51) Int. Cl.
*C12N 5/071*    (2010.01)
*A61K 31/496*   (2006.01)
*A61K 35/28*    (2015.01)
*A61K 35/42*    (2015.01)

(52) U.S. Cl.
CPC .......... *C12N 5/0688* (2013.01); *A61K 31/496* (2013.01); *A61K 35/28* (2013.01); *A61K 35/42* (2013.01); *C12N 2501/065* (2013.01); *C12N 2501/999* (2013.01); *C12N 2506/27* (2013.01)

(58) Field of Classification Search
CPC ............ C12N 5/0688; C12N 2502/065; C12N 2502/999; C12N 2502/27; A61K 31/496; A61K 35/28; A61K 35/42
See application file for complete search history.

(56) References Cited

U.S. PATENT DOCUMENTS

2015/0250824 A1* 9/2015 Ma
2015/0322405 A1  11/2015 Han et al.

FOREIGN PATENT DOCUMENTS

WO    2014/138488 A1    9/2014
WO    2015/038704 A1    3/2015

OTHER PUBLICATIONS

Vedadi et al. A chemical proble selectively inhibits G9a and GLP methyltransferase activity in cells, Nature Chemical Biology, 7: 566-574 (1-16 in provided manuscript) (Year: 2011).*
Huang et al. Efficient generation of lung and airway epithelial cells from human pluripotent stem cells, Nature Biotechnology, 32(1): 84-91). (Year: 2014).*
Nadkarni et al. Organoids as a model system for studying human lung development and disease, Biochemical and Biophysical Research Communications, 473: 675-682 (Year: 2016).*
Shin et al., BIX-01294-induced autophagy regulates elongation of primary cilia, Biochemical and biophysical research communications, 460: 428-433. (Year: 2015).*
Lee et al., Lung Stem Cell Differentiation in Mice Directed by Endothelial Cells via a BMP4-NFATc1-Thrombospondin-1 Axis, Cell, 156: 440-455. (Year: 2014).*
Pappano et al., The Histone Methyltransferase Inhibitor A-366 Uncovers a Role for G9a/GLP in the Epigenetics of Leukemia, PLoS One, p. 1-13 (Year: 2015).*
Liu et al., Optimization of Cellular Activity of G9a Inhibitors 7-Aminoalkoxy-quinazolines, Journal of Medicinal Chemistry, 54: 6139-6150. (Year: 2011).*
Kubicek, Reversal of H3K9me2 by a Small-Molecule Inhibitor for the G9a Histone Methyltransferase, Molecular Cell Technique, 25: 473-481. (Year: 2007).*
Sedmak et al., Intraflagellar transport proteins in ciliogenesis of photoreceptor cells, Biology of the Cell, 103: 449-460. (Year: 2011).*
Ding et al., "The histone H3 methyltransferase G9A epigenetically activates the serine-glycine synthesis pathway to sustain cancer cell survival and proliferation", Cell Metabolism 896-907 (2013).
Green et al. "Generation of anterior foregut endoderm from human embryonic and induced pluripotent stem cells." Nature biotechnology 29.3 (2011): 267-272.
Longmire et al. "Efficient derivation of purified lung and thyroid progenitors from embryonic stem cells." Cell stem cell 10.4 (2012): 398-411.
Mou et al. "Generation of multipotent lung and airway progenitors from mouse ESCs and patient-specific cystic fibrosis iPSCs." Cell stem cell 10.4 (2012): 385-397.
Rock et al. "Basal cells as stem cells of the mouse trachea and human airway epithelium." Proceedings of the National Academy of Sciences 106.31 (2009): 12771-12775.

* cited by examiner

*Primary Examiner* — Arthur S Leonard
*Assistant Examiner* — Joseph Paul Miano
(74) *Attorney, Agent, or Firm* — Nixon Peabody LLP; David S. Resnick; Nicole D. Kling

(57) ABSTRACT

Described herein are methods and compositions relating to the provision and/or differentiation of certain fully differentiated lung cell types, including surfactant producing cells (e.g. club secretory cells), mucus producing (Goblet) cells, mucus-producing goblet like cells, and beating ciliated cells. In some embodiments, one or more of the differentiated lung cell types is present in an organoid. Differentiation of these lung cell types can be induced by contacting lung stem and/or progenitor cells with one or more inhibitors of H3K9me1/2 methyltransferase, e.g., an inhibitor of G9a and/or G1p (EMHT2 and/or EHMT1).

10 Claims, 6 Drawing Sheets

METHODS AND COMPOSITIONS RELATING TO LUNG CELL DIFFERENTIATION

CROSS-REFERENCE TO RELATED APPLICATIONS

This application is a 35 U.S.C. 8 371 National Phase Entry Application of International Application No. PCT/US2017/036530 filed Jun. 8, 2017, which designates the U.S. and claims benefit under 35 U.S.C. § 119 (e) of U.S. Provisional Application No. 62/350,237 filed Jun. 15, 2016, the contents of which are incorporated herein by reference in their entireties.

GOVERNMENT SUPPORT

This invention was made with government support under Grant Nos. R01 HL090136, U01 HL100402, and R01 HL125821 awarded by the National Institutes of Health. The government has certain rights in the invention.

TECHNICAL FIELD

The technology described herein relates to the production of organoids, e.g., lung organoids in vitro.

BACKGROUND

Lung stem and progenitor cells can be differentiation in vitro, but existing protocols for differentiation provide organoids that are limited in their diversity of mature cell types. In order to provide meaningful in vitro systems and models, it is necessary to obtain organoids that contain multiple mature cell types, more accurately representing lung tissue.

SUMMARY

As described herein, the inventors have discovered that inhibiting the activity of certain enzymes (e.g., H3K9me1/2 methyltransferase) during in vitro differentiation permits a population of stem and progenitor cells to give rise to a number of different fully differentiated cell types in the same culture. In one aspect of any of the embodiments, described herein is a method comprising contacting lung stem and/or progenitor cells with an inhibitor of H3K9me1/2 methyltransferase. In some embodiments of any of the aspects, the inhibitor of a H3K9me1/2 methyltransferase is an inhibitor of G9a and/or G1p (EMHT2 and/or EHMT1). In some embodiments of any of the aspects, the inhibitor is selected from the group consisting of: UNC0638; UNC0642; UNC0646; UNC0224; BIX 01294; and A-366. In some embodiments of any of the aspects, the inhibitor is present at a concentration of from about 50 nM to about 500 nM. In some embodiments of any of the aspects, the inhibitor is present at a concentration of about 250 nM. In some embodiments of any of the aspects, the lung stem and/or progenitor cells differentiate to form cells selected from the group consisting of: beating multiciliated cells; mucus-producing goblet like cells; and P63+ Kertatin 5+ cells. In some embodiments of any of the aspects, the lung stem and/or progenitor cells differentiate to form lung organoids comprising surfactant producing cells (e.g., secretory cells and/or club cells), mucus producing cells (e.g., Goblet cells and/or ciliated cells).

In one aspect of any of the embodiments, described herein is a composition comprising a lung cell and an inhibitor of H3K9me1/2 methyltransferase. In some embodiments of any of the aspects, the lung cell is an isolated lung cell. In some embodiments of any of the aspects, the lung cell is a lung stem or progenitor cell. In some embodiments of any of the aspects, the inhibitor of a H3K9me1/2 methyltransferase is an inhibitor of G9a and/or G1p. In some embodiments of any of the aspects, the inhibitor is selected from the group consisting of: UNC0638; UNC0642; UNC0646; UNC0224; BIX 01294; and A-366. In some embodiments of any of the aspects, the inhibitor is present at a concentration of from about 50 nM to about 500 nM. In some embodiments of any of the aspects, the inhibitor is present at a concentration of about 250 nM.

DETAILED DESCRIPTION

Figure 1:
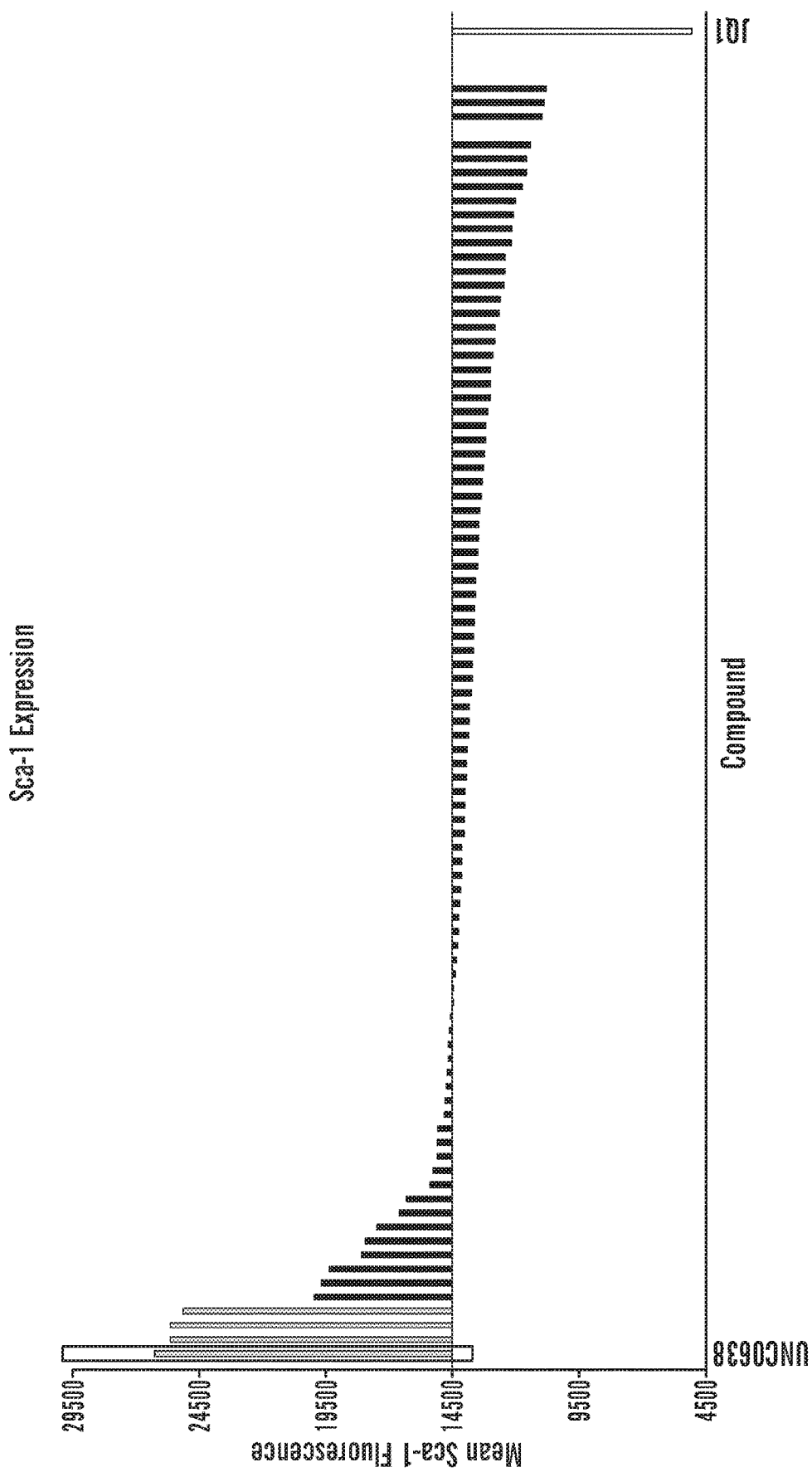
FIG. 1 demonstrates that inhibition of chromatin regulators can alter stem cell surface marker expression in TPC cell lines. The graph shows the amount of stem cell marker Sca-1 on the surface of CK1750 cells after treatment with a library of chemicals. The X axis crosses at the level of Sca-1 fluorescence measured in cells with the vehicle only control (DMSO). Bars up thus represent an increase in Sca-1 and Bars down represent a decrease. Each bar represents a different chemical treatment.

As described herein, the inventors have discovered that inhibition of at least one H3K9me1/2 methyltransferase during differentiation of lung cells in vitro promotes the formation of organoids that comprise of surfactant producing cells (e.g. club secretory cells), mucus producing (Goblet) cells and beating ciliated cells. This is in contrast to earlier methods, which were not able to reliably provide a population of organoids that contained all of these cell types in each organoid. The mammalian airway epithelium (the cell layer lining the bronchioles and trachea) comprises a mixture of cells with specialized functions. Goblet cells produce a protective layer of mucus over the epithelia to prevent damage from inhaled particles. Surfactant releasing cells are required to solubilize the mucus so it can flow readily. Cells with beating cilia keep the mucus layer moving and prevent a mucus buildup that can become infect or obstruct the airways. Critically, the function of each cell type is dependent upon the others. Producing organoids containing all these cell types allows investigators to interrogate not only factors and conditions that influence which of these cells can grow and proliferate, but also the functionality of these cells. Many diseases, including the most common forms of cystic fibrosis arise not from total absence of a particular cell type but from the inability of those cells to function correctly. The organoids described herein, comprising of surfactant producing cells, mucus producing cells and ciliated cells therefore offer a much more physiologically relevant model of lung tissue.

In one aspect of any of the embodiments, described herein is a method comprising contacting lung stem and/or progenitor cells with an inhibitor of H3K9me1/2 methyltransferase. As used herein, "H3K9me1/2 methyltransferase" refers to enzymes that catalyse the transfer of 1 and/or 2 methyl groups to H3 histones at K9.

As used herein, "G9a," "EMHT2," or "euchromatic histone lysine methyltransferase 2" catalyses the dimethylated state of H3K9me2. Sequences for G9a are known for a number of species, e.g., human G9a (NCBI Gene ID No: 10919) mRNA (e.g., NCBI Ref Seqs: NM_001289413.1; NM_001318833.1; NM_006709.4; and NM_025256.6) and protein (e.g., NCBI Ref Seqs: NP_001276342.1; NP_001305762.1; NP_006700.3; and NP_079532.5).

As used herein, "G1p," "G9a-like protein," "EHMT1," or "euchromatic histone lysine methyltransferase 2" also catalyses the dimethylated state of H3K9me2. Sequences for G9a are known for a number of species, e.g., human G1p (NCBI Gene ID No: 79813) mRNA (e.g., NCBI Ref Seqs: NM_001145527.1 and NM_024757.4) and protein (e.g., NCBI Ref Seqs: NP_001138999.1 and NP_079033.4).

In some embodiments of any of the aspects, an inhibitor of H3K9me1/2 methyltransferase can inhibit G9a. In some embodiments of any of the aspects, an inhibitor of H3K9me1/2 methyltransferase can specifically inhibit G9a, e.g., inhibit G9a but not other H3K9me1/2 methyltransferases. In some embodiments of any of the aspects, an inhibitor of H3K9me1/2 methyltransferase can inhibit G1p. In some embodiments of any of the aspects, an inhibitor of H3K9me1/2 methyltransferase can specifically inhibit G1p, e.g., inhibit G1p but not other H3K9me1/2 methyltransferases. In some embodiments of any of the aspects, an inhibitor of H3K9me1/2 methyltransferase can inhibit both G9a and G1p.

As used herein, the term "inhibitor" refers to an agent which can decrease the expression and/or activity of a H3K9me1/2 methyltransferase, e.g. by at least 10% or more, e.g. by 10% or more, 50% or more, 70% or more, 80% or more, 90% or more, 95% or more, or 98% or more. The efficacy of an inhibitor of one or more H3K9me1/2 methyltransferases, e.g. its ability to decrease the level and/or activity of the target can be determined, e.g. by measuring the level of an expression product of the target and/or the activity of the target. Methods for measuring the level of a given mRNA and/or polypeptide are known to one of skill in the art, e.g. RT-PCR with primers can be used to determine the level of RNA and Western blotting with an antibody (e.g. an anti-G9a antibody, e.g. Cat No. ab 185050: Abcam: Cambridge, MA) can be used to determine the level of a polypeptide. The activity of, e.g. a H3K9me1/2 methyltransferase can be determined using methods known in the art, e.g. using commercially available kits for G9a activity (e.g. Cat No. 52001L: BPS Bioscience, San Diego, CA). In some embodiments, the inhibitor can be an inhibitory nucleic acid: an aptamer: an antibody reagent: an antibody: or a small molecule.

In some embodiments of any of the aspects, a cell can be contacted with one inhibitor of H3K9me1/2 methyltransferase. In some embodiments of any of the aspects, a cell can be contacted with two or more inhibitors of H3K9me1/2 methyltransferase.

In some embodiments of the various aspects, the inhibitor of H3K9me1/2 methyltransferase is a compound of Formula (I'):

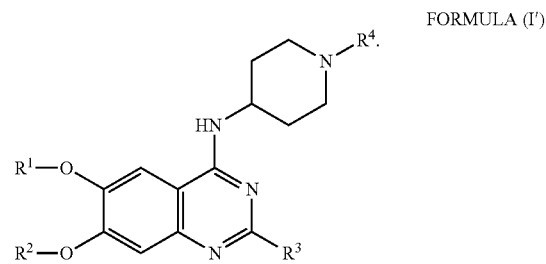

FORMULA (I')

The $R^1$ group in compounds of Formula (I') can be an H, linear or branched alkyl, linear or branched alkenyl, linear or branched alkynyl, cyclyl, heterocyclyl, aryl or heteroaryl, where the alkyl, alkenyl, alkynyl, cyclyl, heterocyclyl, aryl or heteroaryl can be optionally substituted with 1, 2, 3, or 4 independently selected substituents. In some embodiments, $R^1$ is an optionally substituted linear or branched $C_1$-$C_6$ alkyl. Exemplary $C_1$-$C_6$ alkyls for the $R^1$ group include, but are not limited to methyl, ethyl, propyl, isopropyl, butyl, t-butyl, pentyl and hexyl. In some embodiments, $R^1$ is methyl.

The $R^2$ group in compounds of Formula (I') can be an H, linear or branched alkyl, linear or branched alkenyl, linear or branched alkynyl, cyclyl, heterocyclyl, aryl or heteroaryl, where the alkyl, alkenyl, alkynyl, cyclyl, heterocyclyl, aryl or heteroaryl can be optionally substituted with 1, 2, 3, or 4 independently selected substituents. In some embodiments, $R^2$ is an optionally substituted linear or branched $C_1$-$C_6$ alkyl. In some embodiments, $R^2$ is —$(CH_2)_n$—$R^5$, where $R^5$ is H, amine, alkylamine, dialkylamine or an heterocyclyl comprising a nitrogen atom, where the alkylamine, dialkylamine and the heterocyclyl can be optionally substituted with 1, 2, 3 or 4 independently selected substituents; and n is 1, 2, 3, 4, 5, 6. In some embodiments, n is 3.

In various embodiments, $R^5$ can be —$N(R^6)(R^7)$, where $R^6$ and $R^7$ are independently optionally substituted linear or branched $C_1$-$C_6$ alkyl. Without limitations, $R^6$ and $R^7$ can be same or different. In some embodiments, $R^6$ and $R^7$ are selected independently from the group consisting of methyl, ethyl, propyl, isopropyl, butyl, t-butyl, pentyl and hexyl. In one embodiment, $R^6$ and $R^7$ are methyl. In some other embodiments, $R^5$ can be a 3-8 membered heterocyclyl comprising a nitrogen atom and the heterocyclyl can be optionally substituted with 1, 2, 3, or 4 independently selected substituents. In some embodiments, $R^5$ is a 4-6 membered heterocyclyl comprising a nitrogen atom and the heterocyclyl can be optionally substituted with 1, 2, 3 or 4 independently selected substituents. In various embodiments, $R^5$ is

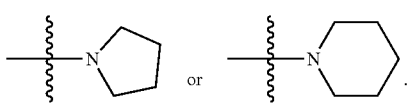 or .

In some embodiments, $R^2$ is selected from the group consisting of

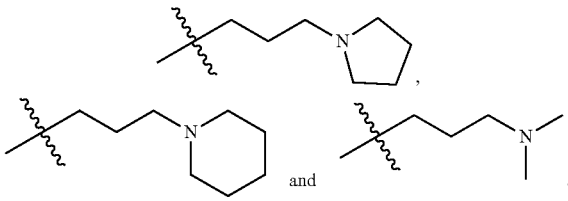

In one embodiment, n is 1 and $R^5$ is H, i.e., $R^2$ is methyl.

The $R^3$ group in compounds of Formula (I') can be an H, linear or branched alkyl, linear or branched alkenyl, linear or branched alkynyl, cyclyl, heterocyclyl, aryl or heteroaryl, where the alkyl, alkenyl, alkynyl, cyclyl, heterocyclyl, aryl or heteroaryl can be optionally substituted with 1, 2, 3, or 4 independently selected substituents. In some embodiments, $R^3$ is a 3-8 membered cyclyl, optionally substituted with 1, 2, 3 or 4 independently selected substituents. Exemplary 3-8 membered cyclyl groups for $R^3$ include, but are not limited to cyclopropyl, cyclobutyl, cyclopentyl and cyclohexyl.

In some embodiments, $R^3$ is a 3-8 membered heterocyclyl comprising 1 or 2 nitrogen atoms, optionally substituted with 1, 2, 3 or independently selected substituents. In some embodiments, $R^3$ is a piperidinyl, optionally substituted with 1 or 2 substituents selected from the group consisting of halo, OH, $C_1$-$C_6$ alkyl, $C_1$-$C_6$alkoxy, $CF_3$, CN, $NO_2$ and carboxyl. In one embodiment, $R^3$ is piperidinyl or 4-difluoropiperidinyl.

In some embodiments, $R^3$ is a 1,4-diazepane, optionally substituted with 1 or 2 independently selected substituents. In some embodiments, $R^3$ is a 1,4-diazepan-1-yl, optionally substituted at the nitrogen with a linear or branched $C_1$-$C_6$ alkyl group. In various embodiments, $R^3$ is 4-methyl-1,4-diazepan-1-yl or 4-isopropyl-1,4-diazepan-1-yl.

In some embodiments, $R^3$ is selected from the group consisting of

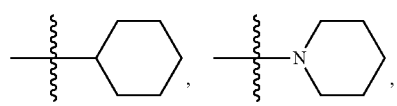

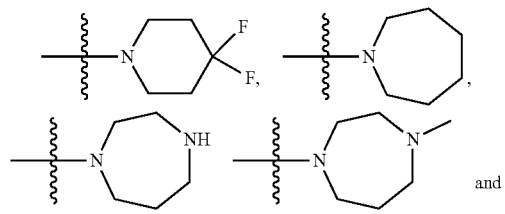 and

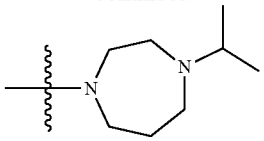

The $R^4$ group in compounds of Formula (I') can be H, linear or branched alkyl, linear or branched alkenyl, linear or branched alkynyl, cyclyl, heterocyclyl, aryl or heteroaryl, where the alkyl, alkenyl, alkynyl, cyclyl, heterocyclyl, aryl or heteroaryl can be optionally substituted with 1, 2, 3, or 4 independently selected substituents.

In some embodiments, $R^4$ is an optionally substituted linear or branched $C_1$-$C_6$ alkyl. Exemplary $C_1$-$C_6$ alkyls for the $R^4$ group include, but are not limited to methyl, ethyl, propyl, isopropyl, butyl, t-butyl, pentyl and hexyl. In some embodiments, $R^1$ is isopropyl.

In some other embodiments, $R^5$ is a 3-8 membered cyclyl, optionally substituted with 1, 2, 3 or 4 independently selected substituents. Exemplary 3-8 membered cyclyl groups for $R^5$ include, but are not limited to, cyclopropyl, cyclybutyl, cyclpentyl and cyclohexyl. In one embodiment, $R^4$ is cyclohexyl.

In yet some other embodiments, $R^5$ is a 3-8 membered heterocyclyl comprising 1 or 2 nitrogen atoms, optionally substituted with 1, 2, 3 or independently selected substituents. In some embodiments, $R^3$ is piperidin-4-yl, optionally substituted with 1 or 2 substituents selected from the group consisting of halo, $C_1$-$C_6$ alkyl, $C_1$-$C_6$alkoxy, $CF_3$, CN, $NO_2$ and carboxyl. In one embodiment, $R^5$ is piperidin-4-yl or N-methyl-piperidn-4-yl.

In still some other embodiments, $R^4$ is-$CH_2R^6$, where $R^6$ is cyclyl, heterocyclyl, aryl or heteroaryl, where the cyclyl, heterocyclyl, aryl or heteroaryl can be optionally substituted with 1, 2, 3, or 4 independently selected substituents. In some embodiments, $R^6$ is a 5-8 membered aryl, optionally substituted with 1 or 2 substituents selected independently from the group consisting of halo, OH, $C_1$-$C_6$ alkyl, $C_1$-$C_6$alkoxy, $CF_3$, CN, $NO_2$ and carboxyl. In one embodiment, $R^6$ is a phenyl, optionally substituted with 1 or 2 substituents.

In some embodiments, $R^5$ is selected from the group consisting of isopropyl, cyclohexyl, piperdin-4-yl, N-methyl-piperidin-4-yl and benzyl.

Compounds of Formula (I') can be synthesized following synthetic methods known in the art or obtained from commercial sources, such as Sigma Aldrich (St. Louis, MO) and Tocris (Bristol, UK). Exemplary methods of preparing compounds of Formula (I') are described, for example, in U.S. Pat. Nos. 3,635,979; 3,853,873; 3,960,861; 4,639,453; 5,064,833; and 5,444,062, content of all of which is incorporated herein by reference in their entireties.

In some embodiments of any of the aspects, the inhibitor of H3K9me1/2 methyltransferase can be UNC0638; UNC0642; UNC0646; UNC0224; BIX 01294; and/or A-366.

UNC0638 has the structure of Formula I and is commercially available, e.g., Cat No. U4885 from Sigma Aldrich (St. Louis, MO).

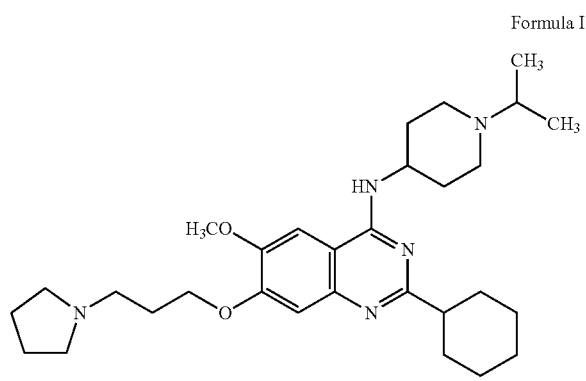 [SMILES: COc1cc2c(NC3CCN(C(C)C)CC3)nc(C3CCCCC3)nc2cc1OCCCN1CCCC1]

Formula I

UNC0642 has the structure of Formula II and is commercially available, e.g., Cat No. SML1037 from Sigma Aldrich (St. Louis, MO).

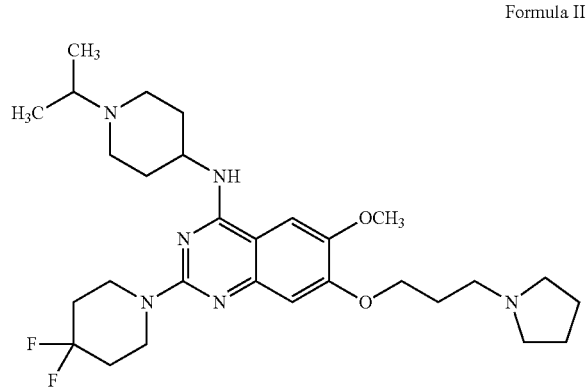 [SMILES: COc1cc2c(NC3CCN(C(C)C)CC3)nc(N3CCC(F)(F)CC3)nc2cc1OCCCN1CCCC1]

Formula II

UNC0646 has the structure of Formula III and is commercially available, e.g., Cat No. SML0633 from Sigma Aldrich (St. Louis, MO).

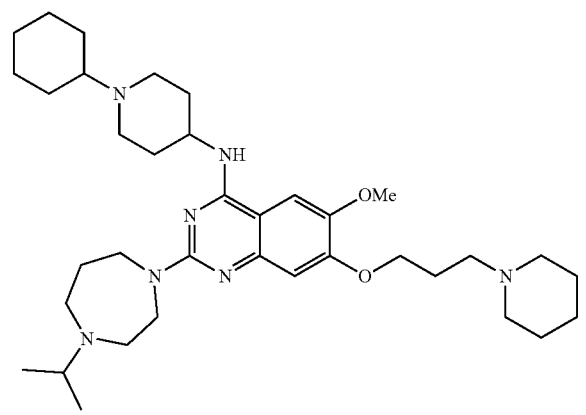

Formula III

UNC0224 has the structure of Formula IV and is commercially available, e.g., Cat No. 3861 from Tocris (Bristol, UK).

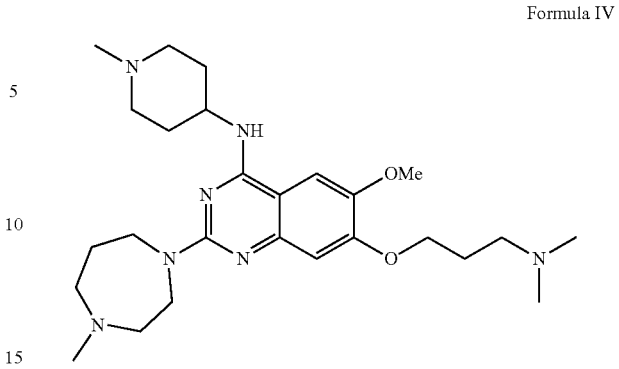

Formula IV

BIX 01294 has the structure of Formula V and is commercially available, e.g., Cat No. B9311 from Sigma Aldrich (St. Louis, MO).

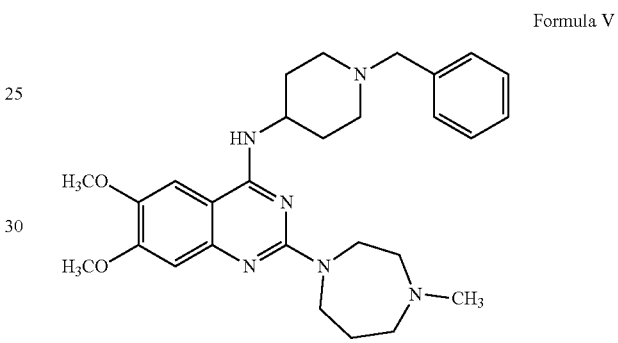

Formula V

A366 has the structure of Formula VI and is commercially available, e.g., Cat No. SML1410 from Sigma Aldrich (St. Louis, MO).

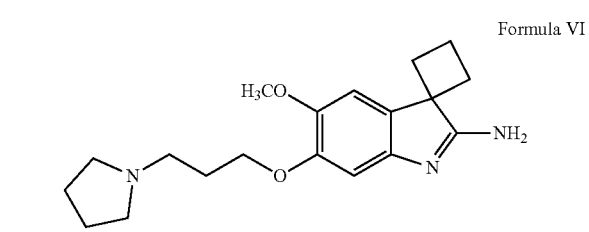 [SMILES: COc1cc2c(cc1OCCCN1CCCC1)N=C(N)C21CCC1]

Formula VI

In some embodiments of any of the aspects, the inhibitor of H3K9me1/2 methyltransferase is present in the cell culture at a concentration of from about 50 nM to about 500 nM. In some embodiments of any of the aspects, the inhibitor of H3K9me1/2 methyltransferase is UNC0638; UNC0642; UNC0646; UNC0224; BIX 01294; and/or A-366 and each inhibitor is present in the cell culture at a concentration of from about 50 nM to about 500 nM. In some embodiments of any of the aspects, the inhibitor of H3K9me1/2 methyltransferase is UNC0638; UNC0642; UNC0646; UNC0224; BIX 01294; and/or A-366 and the inhibitors are present in the cell culture at a total collective concentration of from about 50 nM to about 500 nM. In some embodiments of any of the aspects, the inhibitor of H3K9me1/2 methyltransferase is present in the cell culture at a concentration of from 50 nM to 500 nM. In some embodiments of any of the aspects, the inhibitor of H3K9me1/2 methyltransferase is UNC0638; UNC0642; UNC0646; UNC0224; BIX 01294; and/or A-366 and each inhibitor is present in the cell culture at a concentration of from 50 nM to 500 nM. In some embodiments of any of the aspects, the inhibitor of H3K9me1/2 methyltransferase is UNC0638; UNC0642; UNC0646; UNC0224; BIX 01294; and/or A-366 and inhibitors are present in the cell culture at a total collective concentration of from 50 nM to 500 nM.

In some embodiments of any of the aspects, the inhibitor of H3K9me1/2 methyltransferase is present in the cell culture at a concentration of about 250 nM. In some embodiments of any of the aspects, the inhibitor of H3K9me1/2 methyltransferase is UNC0638; UNC0642; UNC0646; UNC0224; BIX 01294; and/or A-366 and each inhibitor is present in the cell culture at a concentration of about 250 nM. In some embodiments of any of the aspects, the inhibitor of H3K9me1/2 methyltransferase is UNC0638; UNC0642; UNC0646; UNC0224; BIX 01294; and/or A-366 and the inhibitors are present in the cell culture at a total collective concentration of about 250 nM. In some embodiments of any of the aspects, the inhibitor of H3K9me1/2 methyltransferase is present in the cell culture at a concentration of 250 nM. In some embodiments of any of the aspects, the inhibitor of H3K9me1/2 methyltransferase is UNC0638; UNC0642; UNC0646; UNC0224; BIX 01294; and/or A-366 and each inhibitor is present in the cell culture at a concentration of 250 nM. In some embodiments of any of the aspects, the inhibitor of H3K9me1/2 methyltransferase is UNC0638; UNC0642; UNC0646; UNC0224; BIX 01294; and/or A-366 and the inhibitors are present in the cell culture at a total collective concentration of 250 nM.

In some embodiments of any of the aspects, the inhibitor of H3K9me1/2 methyltransferase is UNC0638 and is present in the cell culture at a concentration of about 250 nM. In some embodiments of any of the aspects, the inhibitor of H3K9me1/2 methyltransferase is UNC0638 and is present in the cell culture at a concentration of 250 nM.

The methods and compositions described herein relate to lung stem cells and/or lung progenitor cells. As used herein, the term "stem cell" refers to a cell in an undifferentiated or partially differentiated state that has the property of self-renewal and has the developmental potential to naturally differentiate into a more differentiated cell type, without a specific implied meaning regarding developmental potential (i.e., totipotent, pluripotent, multipotent, etc.). By self-renewal is meant that a stem cell is capable of proliferation and giving rise to more such stem cells, while maintaining its developmental potential. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating.

As used herein, "progenitor cells" refers to cells in an undifferentiated or partially differentiated state and that have the developmental potential to differentiate into at least one more differentiated phenotype, without a specific implied meaning regarding developmental potential (i.e., totipotent, pluripotent, multipotent, etc.) and that does not have the property of self-renewal. Accordingly, the term "progenitor cell" refers to any subset of cells that have the developmental potential, under particular circumstances, to differentiate to a more specialized or differentiated phenotype. In some embodiments, the stem or progenitor cells are pluripotent stem cells. In some embodiments, the stem or progenitor cells are totipotent stem cells.

As used herein, a "differentiated cell" refers to a cell that is more specialized in its fate or function than at a previous point in its development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. In the context of cell ontogeny, the adjective "differentiated", or "differentiating" is a relative term. A "differentiated cell" is a cell that has progressed further down the developmental pathway than the cell it is being compared with.

Lung stem cells, as used in the methods described herein, therefore, encompasses all pluripotent cells capable of differentiating into several cell types of the respiratory system, including, but not limited to, pneumocyte type I and type II cells, interalveolar cells, smooth muscle cells, alveoli epithelial cells, endothelial cells and erythrocytes. Lung progenitor cells, as the term is used herein, refer to the subset of lung stem cells that are committed to a particular pulmonary cell lineage and generally do not self-renew, and can be identified, for example by cell surface markers or intracellular proteins. The presence of LSC can be determined by any method known in the art, or phenotypically through the detection of cell surface markers using assays known to those of skill in the art or those described in the elsewhere herein.

In some embodiments of all aspects of the compositions and methods described, the lung stem and/or progenitor cells are derived or isolated from lung tissue samples and/or a lung stem cell line. In one embodiment of all aspects of the compositions and methods described, the lung stem and/or progenitor cells can be isolated using any method known to one of skill in the art or according to the method described herein. For example, fine needle aspiration for a small lung tissue sample from a live subject. In some embodiments of all aspects of the compositions and methods described, the lung stem and/or progenitor cells are derived ex vivo from other cells, such as embryonic stem cells, induced pluripotent stem cells (iPS cells) or adult pluripotent cells. In some embodiments of any of the aspects, the lung stem and/or progenitor cells can be isolated from a subject.

Lung stem and/or progenitor cells can be isolated for lung tissue samples by any method known in the art. Methods of dissociating individual cells from a tissue sample are known in the art, e.g., in U.S. Pat. No. 7,547,674 and U. S. Patent Application U. S. 2006/0239983, 2009/0148421, and 2009/0180998. These references are herein incorporated by reference in their entirety.

In some embodiments of any of the aspects, the lung stem and/or progenitor cells can be bronchioalveolar stem cells (BASCs). BASCs are readily identified by one of skill in the art, e.g., by use of the cell markers Clara; CCSP; and SPC, see, e.g., Lee et al. Cell 2014 156:440-455; which is incorporated by reference herein in its entirety The methods described herein relate to differentiation of lung stem and/or progenitor cells to form organoids, e.g., organoids comprising both surfactant producing cells (e.g., secretory cells and/or club cells) and mucus producing cells (e.g., Goblet cells) and ciliated cells. These cell types are readily identified by phenotype and/or cell markers known in the art (e.g., by Immunofluorescence, histochemical staining, and/or FACS analysis). For example, ciliated cells are positive for acetylated tubulin and FOXJ1 and negative for CCSP, and Muc5a, Alician Blue, PAS. Club cells are positive for CCSP and negative for Acetylated tubulin, FOXJ1, Muc5a, Alician Blue, PAS. Goblet cells are positive for Muc5a Alician Blue and PAS, negative for FOXJI and acetylated tubulin, and may or may not be positive for CCSP. In some embodiments of any of the aspects, the organoids formed according to the methods described herein can comprise cells selected from beating multiciliated cells; mucus-producing goblet like cells; and/or P63+ Kertatin 5+ cells.

In some embodiments of any of the aspects, the methods described herein can further comprise culturing the cells under conditions that support differentiation of lung stem and/or progenitor cells, e.g., as described in Lee et al. Cell 2014 156:440-455; which is incorporated by reference herein in its entirety. In some embodiments of any of the aspects, the contacting step of methods described herein can occur while the cells are being cultured under conditions that support differentiation of lung stem and/or progenitor cells, e.g., as described in Lee et al. Cell 2014 156:440-455; which is incorporated by reference herein in its entirety.

In some embodiments of any of the aspects, the methods described herein can further comprise the step of selected for lung organoids. In some embodiments of any of the aspects, selecting for lung organoids can comprise size selection or selection for the presence of one or more markers. In some embodiments of any of the aspects, selection for lung organoids can comprise selecting for organoids comprising both surfactant producing cells (e.g., secretory cells and/or club cells) and mucus producing cells (e.g., Goblet cells and/or ciliated cells). In some embodiments of any of the aspects, selection for lung organoids can comprise selecting for organoids comprising cells selected from beating multiciliated cells; mucus-producing goblet like cells; and/or P63+ Kertatin 5+ cells.

In one aspect of any of the embodiments, described herein is a composition comprising a lung cell and an inhibitor of H3K9me1/2 methyltransferase. In some embodiments of any of the aspects, the lung cell is an isolated lung cell. In some embodiments of any of the aspects, the lung cell is a lung stem or progenitor cell.

In some embodiments of any of the aspects, a lung stem or progenitor cell can be a human a lung stem or progenitor cell. In some embodiments of any of the aspects, a lung stem or progenitor cell can be a murine a lung stem or progenitor cell.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one strand nucleic acid of a denatured double-stranded DNA. Alternatively, it can be a single-stranded nucleic acid not derived from any double-stranded DNA. In one aspect, the nucleic acid is DNA. In another aspect, the nucleic acid is RNA. Suitable nucleic acid molecules are DNA, including genomic DNA or cDNA. Other suitable nucleic acid molecules are RNA, including mRNA. The nucleic acid molecule can be naturally occurring, as in genomic DNA, or it may be synthetic, i.e., prepared based up human action, or may be a combination of the two. The nucleic acid molecule can also have certain modification such as 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA), cholesterol addition, and phosphorothioate backbone as described in U.S. patent application No. 20070213292; and certain ribonucleoside that are is linked between the 2'-oxygen and the 4'-carbon atoms with a methylene unit as described in U.S. Pat. No. 6,268,490, wherein both patent and patent application are incorporated hereby reference in their entirety.

Inhibitors of the expression of a given gene can be an inhibitory nucleic acid. In some embodiments, the inhibitory nucleic acid is an inhibitory RNA (iRNA). Double-stranded RNA molecules (dsRNA) have been shown to block gene expression in a highly conserved regulatory mechanism known as RNA interference (RNAi). The inhibitory nucleic acids described herein can include an RNA strand (the antisense strand) having a region which is 30 nucleotides or less in length, i.e., 15-30 nucleotides in length, generally 19-24 nucleotides in length, which region is substantially complementary to at least part the targeted mRNA transcript. The use of these iRNAs enables the targeted degradation of mRNA transcripts, resulting in decreased expression and/or activity of the target.

As used herein, the term "iRNA" refers to an agent that contains RNA as that term is defined herein, and which mediates the targeted cleavage of an RNA transcript via an RNA-induced silencing complex (RISC) pathway. In one embodiment, an iRNA as described herein effects inhibition of the expression and/or activity of a target, e.g. at least one H3K9me1/2 methyltransferase. In certain embodiments, contacting a cell with the inhibitor (e.g. an iRNA) results in a decrease in the target mRNA level in a cell by at least about 5%, about 10%, about 20%, about 30%, about 40%, about 50%, about 60%, about 70%, about 80%, about 90%, about 95%, about 99%, up to and including 100% of the target mRNA level found in the cell without the presence of the iRNA.

In some embodiments, the iRNA can be a dsRNA. A dsRNA includes two RNA strands that are sufficiently complementary to hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of the target. The other strand (the sense strand) includes a region that is complementary to the antisense strand, such that the two strands hybridize and form a duplex structure when combined under suitable conditions. Generally, the duplex structure is between 15 and 30 inclusive, more generally between 18 and 25 inclusive, yet more generally between 19 and 24 inclusive, and most generally between 19 and 21 base pairs in length, inclusive. Similarly, the region of complementarity to the target sequence is between 15 and 30 inclusive, more generally between 18 and 25 inclusive, yet more generally between 19 and 24 inclusive, and most generally between 19 and 21 nucleotides in length, inclusive. In some embodiments, the dsRNA is between 15 and 20 nucleotides in length, inclusive, and in other embodiments, the dsRNA is between 25 and 30 nucleotides in length, inclusive. As the ordinarily skilled person will recognize, the targeted region of an RNA targeted for cleavage will most often be part of a larger RNA molecule, often an mRNA molecule. Where relevant, a "part" of an mRNA target is a contiguous sequence of an mRNA target of sufficient length to be a substrate for RNAi-directed cleavage (i.e., cleavage through a RISC pathway). dsRNAs having duplexes as short as 9 base pairs can, under some circumstances, mediate RNAi-directed RNA cleavage. Most often a target will be at least 15 nucleotides in length, preferably 15-30 nucleotides in length.

In yet another embodiment, the RNA of an iRNA, e.g., a dsRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In particular embodiments, the modified RNA will have a phosphorus atom in its internucleoside backbone.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, each of which is herein incorporated by reference Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, each of which is herein incorporated by reference.

In other RNA mimetics suitable or contemplated for use in iRNAs, both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, each of which is herein incorporated by reference. Further teaching of PNA compounds can be found, for example, in Nielsen et al., Science, 1991, 254, 1497-1500.

Some embodiments featured in the invention include RNAs with phosphorothioate backbones and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2-and-N(CH3)-CH2-CH2-[wherein the native phosphodiester backbone is represented as —O—P—O—CH2-] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH$_2$)nO]mCH3, O(CH2)·nOCH3, O(CH$_2$)nNH2, O(CH$_2$)nCH3, O(CH$_2$)nONH2, and O(CH2)nON [(CH2)nCH3)]2, where n and m are from 1 to about 10. In other embodiments, dsRNAs include one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2' methoxyethoxy (2'-O—CH2CH2OCH3, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)2ON(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'—OCH3), 2'-aminopropoxy (2'-OCH2CH2CH2NH2) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application, and each of which is herein incorporated by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278)

and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,30; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,681,941; 6,015,886; 6,147,200; 6,166,197; 6,222,025; 6,235,887; 6,380,368; 6,528,640; 6,639,062; 6,617,438; 7,045,610; 7,427,672; and 7,495,088, each of which is herein incorporated by reference, and U.S. Pat. No. 5,750,692, also herein incorporated by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) Nucleic Acids Research 33 (1): 439-447; Mook, OR. et al., (2007) Mol Canc Ther 6 (3): 833-843; Grunweller, A. et al., (2003) Nucleic Acids Research 31 (12): 3185-3193). Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, each of which is herein incorporated by reference in its entirety.

Another modification of the RNA of an iRNA featured in the invention involves chemically linking to the RNA one or more ligands, moieties or conjugates that enhance the activity, cellular distribution, pharmacokinetic properties, or cellular uptake of the iRNA. Such moieties include but are not limited to lipid moieties such as a cholesterol moiety (Letsinger et al., Proc. Natl. Acid. Sci. USA, 1989, 86:6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero-3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

In some embodiments, a nucleic acid as described herein is comprised by a vector. In some of the aspects described herein, a nucleic acid sequence as described herein, or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification. The term "expression" refers to the cellular processes involved in producing RNA and proteins and as appropriate, secreting proteins, including where applicable, but not limited to, for example, transcription, transcript processing, translation and protein folding, modification and processing. "Expression products" include RNA transcribed from a gene, and polypeptides obtained by translation of mRNA transcribed from a gene. The term "gene" means the nucleic acid sequence which is transcribed (DNA) to RNA in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "viral vector" refers to a nucleic acid vector construct that includes at least one element of viral origin and has the capacity to be packaged into a viral vector particle. The viral vector can contain the nucleic acid encoding encoding a polypeptide as described herein in place of non-essential viral genes. The vector and/or particle may be utilized for the purpose of transferring any nucleic acids into cells either in vitro or in vivo. Numerous forms of viral vectors are known in the art.

By "recombinant vector" is meant a vector that includes a heterologous nucleic acid sequence, or "transgene" that is capable of expression in vivo. It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

In some embodiments, an inhibitor of a given polypeptide can be an antibody reagent specific for that polypeptide. As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody reagent" refers to a polypeptide that includes at least one immunoglobulin variable domain or immunoglobulin variable domain sequence and which specifically binds a given antigen. An antibody reagent can comprise an antibody or a polypeptide comprising an antigen-binding domain of an antibody. In some embodiments, an antibody reagent can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody reagent" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26 (3): 629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917; which are incorporated by reference herein in their entireties). Each VH and VL is typically composed of three CDRs and four FRs, arranged from amino-terminus to carboxy-terminus in the following order: FR1, CDR1, FR2, CDR2, FR3, CDR3, FR4.

The terms "antigen-binding fragment" or "antigen-binding domain", which are used interchangeably herein are used to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality.

As used herein, the term "specific binding" refers to a chemical interaction between two molecules, compounds, cells and/or particles wherein the first entity binds to the second, target entity with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third nontarget entity. A reagent specific for a given target is one that exhibits specific binding for that target under the conditions of the assay being utilized.

As used herein, "expression level" refers to the number of mRNA molecules and/or polypeptide molecules encoded by a given gene that are present in a cell or sample. Expression levels can be increased or decreased relative to a reference level.

As used herein, "contacting" refers to any suitable means for delivering, or exposing, an agent to at least one cell. Exemplary delivery methods include, but are not limited to, direct delivery to cell culture medium, perfusion, injection, or other delivery method well known to one skilled in the art.

The term "somatic stem cell" is used herein to refer to any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, mesenchymal stem cells and hematopoietic stem cells. In some embodiments, the stem or progenitor cells can be embryonic stem cells. As used herein, "embryonic stem cells" refers to stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are totipotent cells derived from the early embryo or blastocyst. Embryonic stem cells can be obtained directly from suitable tissue, including, but not limited to human tissue, or from established embryonic cell lines. In one embodiment, embryonic stem cells are obtained as described by Thomson et al. (U.S. Pat. Nos. 5,843,780 and 6,200,806; Science 282:1145, 1998; Curr. Top. Dev. Biol. 38:133 ff, 1998; Proc. Natl. Acad. Sci. U.S.A. 92:7844, 1995 which are incorporated by reference herein in their entirety).

Exemplary stem cells include induced pluriopotent stem cells, embryonic stem cells, adult stem cells, pluripotent stem cells, lung stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96 (25): 14482 86, 1999; Zuk et al., Tissue Engineering, 7:211 228, 2001 ("Zuk et al."); Atala et al., particularly Chapters 33 41; and U.S. Pat. Nos. 5,559,022, 5,672,346 and 5,827,735.

As used herein, the term "alkyl" means a straight or branched, saturated aliphatic radical having a chain of carbon atoms. $C_x$ alkyl and $C_x$-$C_y$ alkyl are typically used where X and Y indicate the number of carbon atoms in the chain. For example, $C_1$-$C_6$ alkyl includes alkyls that have a chain of between 1 and 6 carbons (e.g., methyl, ethyl, propyl, isopropyl, butyl, sec-butyl, isobutyl, tert-butyl, pentyl, neopentyl, hexyl, and the like). Alkyl represented along with another radical (e.g., as in arylalkyl) means a straight or branched, saturated alkyl divalent radical having the number of atoms indicated or when no atoms are indicated means a bond, e.g., ($C_6$-$C_{10}$) aryl ($C_0$-$C_3$)alkyl includes phenyl, benzyl, phenethyl, 1-phenylethyl 3-phenylpropyl, and the like. Backbone of the alkyl can be optionally inserted with one or more heteroatoms, such as N, O, or S.

In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Likewise, preferred cycloalkyls have from 3-10 carbon atoms in their ring structure, and more preferably have 5, 6 or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

Substituents of a substituted alkyl can include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —CF3, —CN and the like.

As used herein, the term "alkenyl" refers to unsaturated straight-chain, branched-chain or cyclic hydrocarbon radicals having at least one carbon-carbon double bond. $C_x$ alkenyl and $C_x$-$C_y$alkenyl are typically used where X and Y indicate the number of carbon atoms in the chain. For example, $C_2$-$C_6$alkenyl includes alkenyls that have a chain of between 1 and 6 carbons and at least one double bond, e.g., vinyl, allyl, propenyl, isopropenyl, 1-butenyl, 2-butenyl, 3-butenyl, 2-methylallyl, 1-hexenyl, 2-hexenyl, 3-hexenyl, and the like). Alkenyl represented along with another radical (e.g., as in arylalkenyl) means a straight or branched, alkenyl divalent radical having the number of atoms indicated. Backbone of the alkenyl can be optionally inserted with one or more heteroatoms, such as N, O, or S.

As used herein, the term "alkynyl" refers to unsaturated hydrocarbon radicals having at least one carbon-carbon triple bond. $C_x$ alkynyl and $C_x$-$C_y$alkynyl are typically used where X and Y indicate the number of carbon atoms in the chain. For example, $C_2$-$C_6$alkynyl includes alkynls that have a chain of between 1 and 6 carbons and at least one triple bond, e.g., ethynyl, 1-propynyl, 2-propynyl, 1-butynyl, isopentynyl, 1,3-hexa-diyn-yl, n-hexynyl, 3-pentynyl, 1-hexen-3-ynyl and the like. Alkynyl represented along with another radical (e.g., as in arylalkynyl) means a straight or branched, alkynyl divalent radical having the number of atoms indicated. Backbone of the alkynyl can be optionally inserted with one or more heteroatoms, such as N, O, or S.

The terms "alkylene," "alkenylene," and "alkynylene" refer to divalent alkyl, alkelyne, and alkynylene" radicals.

As used herein, the term "alkylidene" means a straight or branched unsaturated, aliphatic, divalent radical having a general formula=$CR_aR_b$. $C_x$ alkylidene and $C_x$-$C_y$alkylidene are typically used where X and Y indicate the number of carbon atoms in the chain. For example, $C_2$-$C_6$alkylidene includes methylidene (=$CH_2$), ethylidene (=$CHCH_3$), isopropylidene (=$C(CH_3)_2$), propylidene (=$CHCH_2CH_3$), allylidene (=$CH$—$CH$=$CH_2$), and the like).

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

As used herein, the term "halogen" or "halo" refers to an atom selected from fluorine, chlorine, bromine and iodine. The term "halogen radioisotope" or "halo isotope" refers to a radionuclide of an atom selected from fluorine, chlorine, bromine and iodine.

A "halogen-substituted moiety" or "halo-substituted moiety", as an isolated group or part of a larger group, means an aliphatic, alicyclic, or aromatic moiety, as described herein, substituted by one or more "halo" atoms, as such terms are defined in this application. For example, halo-substituted alkyl includes haloalkyl, dihaloalkyl, trihaloalkyl, perhaloalkyl and the like (e.g. halosubstituted ($C_1$-$C_3$)alkyl includes chloromethyl, dichloromethyl, difluoromethyl, trifluoromethyl (—$CF_3$), 2,2,2-trifluoroethyl, perfluoroethyl, 2,2,2-trifluoro-1,1-dichloroethyl, and the like).

The term "aryl" refers to monocyclic, bicyclic, or tricyclic fused aromatic ring system. $C_x$ aryl and $C_x$-$C_y$aryl are typically used where X and Y indicate the number of carbon atoms in the ring system. Exemplary aryl groups include, but are not limited to, pyridinyl, pyrimidinyl, furanyl, thienyl, imidazolyl, thiazolyl, pyrazolyl, pyridazinyl, pyrazinyl, triazinyl, tetrazolyl, indolyl, benzyl, phenyl, naphthyl, anthracenyl, azulenyl, fluorenyl, indanyl, indenyl, naphthyl, phenyl, tetrahydronaphthyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl, and the like. In some embodiments, 1, 2, 3, or 4 hydrogen atoms of each ring can be substituted by a substituent.

The term "heteroaryl" refers to an aromatic 5-8 membered monocyclic, 8-12 membered fused bicyclic, or 11-14 membered fused tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$ heteroaryl and $C_x$-$C_y$heteroaryl are typically used where X and Y indicate the number of carbon atoms in the ring system. Heteroaryls include, but are not limited to, those derived from benzo[b]furan, benzo[b] thiophene, benzimidazole, imidazo[4,5-c]pyridine, quinazoline, thieno[2,3-c]pyridine, thieno[3,2-b]pyridine, thieno[2, 3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole, 2 (1H)-pyridinone, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. Some exemplary heteroaryl groups include, but are not limited to, pyridyl, furyl or furanyl, imidazolyl, benzimidazolyl, pyrimidinyl, thiophenyl or thienyl, pyridazinyl, pyrazinyl, quinolinyl, indolyl, thiazolyl, naphthyridinyl, 2-amino-4-oxo-3,4-dihydropteridin-6-yl, tetrahydroisoquinolinyl, and the like. In some embodiments, 1, 2, 3, or 4 hydrogen atoms of each ring may be substituted by a substituent.

The term "cyclyl" or "cycloalkyl" refers to saturated and partially unsaturated cyclic hydrocarbon groups having 3 to 12 carbons, for example, 3 to 8 carbons, and, for example, 3 to 6 carbons. $C_x$cyclyl and $C_x$-$C_y$cylcyl are typically used where X and Y indicate the number of carbon atoms in the ring system. The cycloalkyl group additionally can be optionally substituted, e.g., with 1, 2, 3, or 4 substituents. $C_3$-$C_{10}$cyclyl includes cyclopropyl, cyclobutyl, cyclopentyl, cyclohexyl, cyclohexenyl, 2,5-cyclohexadienyl, cycloheptyl, cyclooctyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like.

Aryl and heteroaryls can be optionally substituted with one or more substituents at one or more positions, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). $C_x$heterocyclyl and $C_x$-$C_y$heterocyclyl are typically used where X and Y indicate the number of carbon atoms in the ring system. In some embodiments, 1, 2 or 3 hydrogen atoms of each ring can be substituted by a substituent. Exemplary heterocyclyl groups include, but are not limited to piperazinyl, pyrrolidinyl, dioxanyl, morpholinyl, tetrahydrofuranyl, piperidyl, 4-morpholyl, 4-piperazinyl, pyrrolidinyl, perhydropyrrolizinyl, 1,4-diazaperhydroepinyl, 1,3-dioxanyl, 1,4-dioxanyland the like.

The terms "bicyclic" and "tricyclic" refers to fused, bridged, or joined by a single bond polycyclic ring assemblies.

The term "cyclylalkylene" means a divalent aryl, heteroaryl, cyclyl, or heterocyclyl.

As used herein, the term "fused ring" refers to a ring that is bonded to another ring to form a compound having a bicyclic structure when the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems can be saturated, partially saturated, cyclyl, heterocyclyl, aromatics, heteroaromatics, and the like.

As used herein, the term "carbonyl" means the radical —C(O)—. It is noted that the carbonyl radical can be further substituted with a variety of substituents to form different carbonyl groups including acids, acid halides, amides, esters, ketones, and the like.

The term "carboxy" means the radical —C(O)O—. It is noted that compounds described herein containing carboxy moieties can include protected derivatives thereof, i.e., where the oxygen is substituted with a protecting group. Suitable protecting groups for carboxy moieties include benzyl, tert-butyl, and the like. The term "carboxyl" means —COOH The term "cyano" means the radical —CN.

The term, "heteroatom" refers to an atom that is not a carbon atom. Particular examples of heteroatoms include, but are not limited to nitrogen, oxygen, sulfur and halogens. A "heteroatom moiety" includes a moiety where the atom by which the moiety is attached is not a carbon. Examples of heteroatom moieties include —N=, —NR$^N$—, —N$^+$(O$^-$) =, —O—, —S— or —S(O)$_2$—, —OS(O)$_2$—, and —SS—, wherein R$^N$ is H or a further substituent.

The term "hydroxy" means the radical —OH.

The term "imine derivative" means a derivative comprising the moiety —C(NR)—, wherein R comprises a hydrogen or carbon atom alpha to the nitrogen.

The term "nitro" means the radical —NO$_2$.

An "oxaaliphatic," "oxaalicyclic", or "oxaaromatic" mean an aliphatic, alicyclic, or aromatic, as defined herein, except where one or more oxygen atoms (—O—) are positioned between carbon atoms of the aliphatic, alicyclic, or aromatic respectively.

An "oxoaliphatic," "oxoalicyclic", or "oxoaromatic" means an aliphatic, alicyclic, or aromatic, as defined herein, substituted with a carbonyl group. The carbonyl group can be an aldehyde, ketone, ester, amide, acid, or acid halide.

As used herein, the term, "aromatic" means a moiety wherein the constituent atoms make up an unsaturated ring system, all atoms in the ring system are sp2 hybridized and the total number of pi electrons is equal to 4n+2. An aromatic ring canbe such that the ring atoms are only carbon atoms (e.g., aryl) or can include carbon and non-carbon atoms (e.g., heteroaryl).

As used herein, the term "substituted" refers to independent replacement of one or more (typically 1, 2, 3, 4, or 5) of the hydrogen atoms on the substituted moiety with substituents independently selected from the group of substituents listed below in the definition for "substituents" or otherwise specified. In general, a non-hydrogen substituent can be any substituent that can be bound to an atom of the given moiety that is specified to be substituted. Examples of substituents include, but are not limited to, acyl, acylamino, acyloxy, aldehyde, alicyclic, aliphatic, alkanesulfonamido, alkanesulfonyl, alkaryl, alkenyl, alkoxy, alkoxycarbonyl, alkyl, alkylamino, alkylcarbanoyl, alkylene, alkylidene, alkylthios, alkynyl, amide, amido, amino, amino, aminoalkyl, aralkyl, aralkylsulfonamido, arenesulfonamido, arenesulfonyl, aromatic, aryl, arylamino, arylcarbanoyl, aryloxy, azido, carbamoyl, carbonyl, carbonyls (including ketones, carboxy, carboxylates, CF$_3$, cyano (CN), cycloalkyl, cycloalkylene, ester, ether, haloalkyl, halogen, halogen, heteroaryl, heterocyclyl, hydroxy, hydroxy, hydroxyalkyl, imino, iminoketone, ketone, mercapto, nitro, oxaalkyl, oxo, oxoalkyl, phosphoryl (including phosphonate and phosphinate), silyl groups, sulfonamido, sulfonyl (including sulfate, sulfamoyl and sulfonate), thiols, and ureido moieties, each of which may optionally also be substituted or unsubstituted. In some cases, two substituents, together with the carbon(s) to which they are attached to, can form a ring.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy, n-propyloxy, iso-propyloxy, n-butyloxy, iso-butyloxy, and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. Aroxy can be represented by —O-aryl or O-heteroaryl, wherein aryl and heteroaryl are as defined below. The alkoxy and aroxy groups can be substituted as described above for alkyl.

The term "aralkyl", as used herein, refers to an alkyl group substituted with an aryl group (e.g., an aromatic or heteroaromatic group).

The term "alkylthio" refers to an alkyl group, as defined above, having a sulfur radical attached thereto. In preferred embodiments, the "alkylthio" moiety is represented by one of —S-alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups. "Arylthio" refers to aryl or heteroaryl groups.

The term "sulfinyl" means the radical —SO—. It is noted that the sulfinyl radical can be further substituted with a variety of substituents to form different sulfinyl groups including sulfinic acids, sulfinamides, sulfinyl esters, sulfoxides, and the like.

The term "sulfonyl" means the radical —SO$_2$—. It is noted that the sulfonyl radical can be further substituted with a variety of substituents to form different sulfonyl groups including sulfonic acids (—SO$_3$H), sulfonamides, sulfonate esters, sulfones, and the like.

The term "thiocarbonyl" means the radical —C(S)—. It is noted that the thiocarbonyl radical can be further substituted with a variety of substituents to form different thiocarbonyl groups including thioacids, thioamides, thioesters, thioketones, and the like.

As used herein, the term "amino" means —NH$_2$. The term "alkylamino" means a nitrogen moiety having at least one straight or branched unsaturated aliphatic, cyclyl, or heterocyclyl radicals attached to the nitrogen. For example, representative amino groups include —NH$_2$, —NHCH$_3$, —N(CH$_3$)$_2$, —NH(C$_1$-C$_{10}$alkyl), —N(C$_1$-C$_{10}$alkyl)$_2$, and the like. The term "alkylamino" includes "alkenylamino," "alkynylamino," "cyclylamino," and "heterocyclylamino." The term "arylamino" means a nitrogen moiety having at least one aryl radical attached to the nitrogen. For example —NHaryl, and —N(aryl)$_2$. The term "heteroarylamino" means a nitrogen moiety having at least one heteroaryl radical attached to the nitrogen. For example —NHheteroaryl, and —N(heteroaryl)$_2$. Optionally, two substituents together with the nitrogen can also form a ring. Unless indicated otherwise, the compounds described herein containing amino moieties can include protected derivatives thereof. Suitable protecting groups for amino moieties include acetyl, tertbutoxycarbonyl, benzyloxycarbonyl, and the like.

The term "aminoalkyl" means an alkyl, alkenyl, and alkynyl as defined above, except where one or more substituted or unsubstituted nitrogen atoms (—N—) are positioned between carbon atoms of the alkyl, alkenyl, or alkynyl. For example, an (C$_2$-C$_6$)aminoalkyl refers to a chain comprising between 2 and 6 carbons and one or more nitrogen atoms positioned between the carbon atoms.

The term "alkoxyalkoxy" means —O-(alkyl)-O-(alkyl), such as —OCH$_2$CH$_2$OCH$_3$, and the like.

The term "alkoxycarbonyl" means —C(O)O-(alkyl), such as —C(=O)OCH$_3$, —C(=O)OCH$_2$CH$_3$, and the like.

The term "alkoxyalkyl" means -(alkyl)-O-(alkyl), such as —CH$_2$OCH$_3$, —CH$_2$OCH$_2$CH$_3$, and the like.

The term "aryloxy" means —O-(aryl), such as —O-phenyl, —O-pyridinyl, and the like.

The term "arylalkyl" means -(alkyl)-(aryl), such as benzyl (i.e., —CH$_2$phenyl), —CH$_2$-pyrindinyl, and the like.

The term "arylalkyloxy" means —O-(alkyl)-(aryl), such as —O-benzyl, —O—CH$_2$-pyridinyl, and the like.

The term "cycloalkyloxy" means —O-(cycloalkyl), such as —O-cyclohexyl, and the like.

The term "cycloalkylalkyloxy" means —O-(alkyl)-(cycloalkyl, such as —OCH$_2$cyclohexyl, and the like.

The term "aminoalkoxy" means —O-(alkyl)-NH$_2$, such as —OCH$_2$NH$_2$, —OCH$_2$CH$_2$NH$_2$, and the like.

The term "mono- or di-alkylamino" means —NH (alkyl) or —N(alkyl)(alkyl), respectively, such as —NHCH$_3$, —N(CH$_3$)$_2$, and the like.

The term "mono- or di-alkylaminoalkoxy" means —O-(alkyl)-NH (alkyl) or —O-(alkyl)-N(alkyl) (alkyl), respectively, such as —OCH$_2$NHCH$_3$, —OCH$_2$CH$_2$N(CH$_3$)$_2$, and the like.

The term "arylamino" means —NH (aryl), such as —NH-phenyl, —NH-pyridinyl, and the like.

The term "arylalkylamino" means —NH-(alkyl)-(aryl), such as —NH-benzyl, —NHCH$_2$-pyridinyl, and the like.

The term "alkylamino" means —NH (alkyl), such as —NHCH$_3$, —NHCH$_2$CH$_3$, and the like.

The term "cycloalkylamino" means —NH-(cycloalkyl), such as —NH-cyclohexyl, and the like.

The term "cycloalkylalkylamino" —NH-(alkyl)-(cycloalkyl), such as —NHCH$_2$-cyclohexyl, and the like.

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a C$_1$ alkyl comprises methyl (i.e., —CH3) as well as —CR$_a$R$_b$R$_c$ where R$_a$, R$_b$, and R$_c$ can each independently be hydrogen or any other substituent where the atom alpha to the carbon is a heteroatom or cyano. Hence, CF$_3$, CH$_2$OH and CH$_2$CN are all C$_1$ alkyls.

Unless otherwise stated, structures depicted herein are meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

Pharmaceutically acceptable salts of the compounds of Formula (I') are also included in embodiments of the various aspects described herein. A "pharmaceutically acceptable salt", as used herein, is intended to encompass any compound described herein that is utilized in the form of a salt thereof, especially where the salt confers on the compound improved pharmacokinetic properties as compared to the free form of compound or a different salt form of the compound. The pharmaceutically acceptable salt form can also initially confer desirable pharmacokinetic properties on the compound that it did not previously possess, and may even positively affect the pharmacodynamics of the compound with respect to its therapeutic activity in the body. An example of a pharmacokinetic property that can be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Pharmaceutically acceptable salts include those derived from inorganic acids such as sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like. See, for example, Berge et al., "Pharmaceutical Salts", *J. Pharm. Sci.* 66:1-19 (1977), the content of which is herein incorporated by reference in its entirety. Exemplary salts also include the hydrobromide, hydrochloride, sulfate, bisulfate, phosphate, nitrate, acetate, succinate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. Suitable acids which are capable of forming salts with the compounds of the disclosure include inorganic acids such as hydrochloric acid, hydrobromic acid, perchloric acid, nitric acid, thiocyanic acid, sulfuric acid, phosphoric acid, and the like; and organic acids such as 1,2-ethanedisulfonic acid, 2-hydroxyethanesulfonic acid, 2-naphthalenesulfonic acid, 3-phenylpropionic acid, 4-methylbicyclo[2.2.2]oct-2-ene-1-carboxylic acid, 4,4'-mefhylenebis(3-hydroxy-2-ene-1-carboxylic acid), acetic acid, anthranilic acid, benzenesulfonic acid, benzoic acid, camphorsulfonic acid, cinnamic acid, citric acid, cyclopentanepropionic acid, ethanesulfonic acid, formic acid, fumaric acid, glucoheptonic acid, gluconic acid, glutamic acid, glycolic acid, heptanoic acid, hydroxynaphthoic acid, lactic acid, lauryl sulfuric acid, maleic acid, malic acid, malonic acid, mandelic acid, methanesulfonic acid, muconic acid, naphthalene sulfonic acid, o-(4-hydroxybenzoyl)benzoic acid, oxalic acid, p-chlorobenzenesulfonic acid, propionic acid, p-toluenesulfonic acid, pyruvic acid, salicylic acid, stearic acid, succinic acid, sulfanilic acid, tartaric acid, tertiary butylacetic acid, trifluoroacetic acid, trimethylacetic acid, and the like. Suitable bases capable of forming salts with the compounds of the disclosure include inorganic bases such as sodium hydroxide, ammonium hydroxide, sodium carbonate, calcium hydroxide, potassium hydroxide and the like; and organic bases such as mono-, di- and tri-alkyl and aryl amines (e.g., triethylamine, diisopropyl amine, methyl amine, dimethyl amine, N-methylglucamine, pyridine, picoline, dicyclohexylamine, N,N'-dibezylethylenediamine, and the like), and optionally substituted ethanol-amines (e.g., ethanolamine, diethanolamine, trierhanolamine and the like).

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 19th Edition, published by Merck Sharp & Dohme Corp., 2011 (ISBN 978-O-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), Taylor & Francis Limited, 2014 (ISBN 0815345305, 9780815345305); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, ADA M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method comprising contacting lung stem and/or progenitor cells with an inhibitor of H3K9me1/2 methyltransferase.
2. The method of any of the preceding paragraphs, wherein the inhibitor of a H3K9me1/2 methyltransferase is an inhibitor of G9a and/or G1p (EMHT2 and/or EHMT1).
3. The method of any of the preceding paragraphs, wherein the inhibitor is selected from the group consisting of:
   UNC0638; UNC0642; UNC0646; UNC0224; BIX 01294; and A-366.
4. The method of any of the preceding paragraphs, wherein the inhibitor is present at a concentration of from about 50 nM to about 500 nM.
5. The method of any of the preceding paragraphs, wherein the inhibitor is present at a concentration of about 250 nM.
6. The method of any of the preceding paragraphs, whereby the lung stem and/or progenitor cells differentiate to form cells selected from the group consisting of:
   beating multiciliated cells; mucus-producing goblet like cells; and P63+ Kertatin 5+ cells.
7. The method of any of the preceding paragraphs, whereby the lung stem and/or progenitor cells differentiate to form lung organoids comprising surfactant producing cells (e.g., secretory cells and/or club cells), mucus producing cells (e.g., Goblet cells and/or ciliated cells).

8. A composition comprising a lung cell and an inhibitor of H3K9me1/2 methyltransferase.

9. The composition of paragraph 8, wherein the lung cell is an isolated lung cell.

10. The composition of any of paragraphs 8-9, wherein the lung cell is a lung stem or progenitor cell.

11. The composition of any of paragraphs 8-10, wherein the inhibitor of a H3K9me1/2 methyltransferase is an inhibitor of G9a and/or G1p.

12. The composition of any of paragraphs 7-10, wherein the inhibitor is selected from the group consisting of: UNC0638; UNC0642; UNC0646; UNC0224; BIX 01294; and A-366.

13. The composition of any of paragraphs 7-12, wherein the inhibitor is present at a concentration of from about 50 nM to about 500 nM.

14. The composition of any of paragraphs 7-13, wherein the inhibitor is present at a concentration of about 250 nM.

EXAMPLES

Example 1

Proper epigenetic control of transcription is known to be important for the homeostasis of stem cells and is frequently disrupted in cancer, but this has not been well investigated in lung biology or lung disease. The stem cell marker Sca-1 enriches for mouse bronchioalveolar stem cells (BASCs) and lung adenocarcinoma cells with enhanced metastatic and tumor propagation abilities (TPCs).

A flow cytometry screen of adenocarcinoma cell lines revealed that UNC0638, a small molecule inhibitor of H3K9me1/2 methyltransferases enriches for high Sca-1 expressing, TPC-like cells. Expression analysis of primary adenocarcinomas shows that G9a/G1p are down-regulated in Sca-1+ metastatic TPCs. Furthermore, gene expression analysis of 400+ early stage lung adenocarcinoma patients reveals that low expression of G9a and high expression of KDM3A, an H3K9me1/2 demethylase significantly correlate with worse survival, implying that dysregulation of H3K9me1/2 is a significant factor in human disease.

Interestingly, in transplantation assays, preliminary G9a/G1p inhibition of adenocarcinoma cells increases Sca-1+ cells but does not increase lung tumor burden instead, significantly more tumors are observed in other locations. Whilst inhibition does not affect cell proliferation or migration, colony forming efficiency in 3D organoid culture is significantly increased, suggesting that stem/initiation rather than migratory/invasive mechanisms may underlie the more tumorigenic phenotypes of H3K9me1/2 low, Sca-1+ TPCs.

H3K9me1/2 also regulates the behavior of lung stem cells; G9a/G1p inhibition of BASCs or alveolar type 2 cells in 3D co-culture assays increases Sca-1+ cells and undifferentiated organoids and significantly decreases alveolar-lineage organoids. BASC cultures also show increases in bronchiolar-lineage organoids, implying that cell fate decisions may regulated by H3K9me1/2.

These findings indicate that common mechanisms of epigenetic regulation exist between mouse lung stem cells and lung TPCs.

Example 2

The CK1750 and SC241 cell lines derived from K-ras; p53fl/fl mouse adenocarcinoma tumors are highly enriched for Sca-1 and CD24. These cell lines were screened for factors that alter the expression of Sca1, CD24 or both markers, using the Stem Cell Core's Pilot Known Bioactives library, a small molecule library enriched in inhibitors of chromatin regulators (FIG. 1). UNC0638 treatment caused the largest increase in Sca-1.

Figure 2:
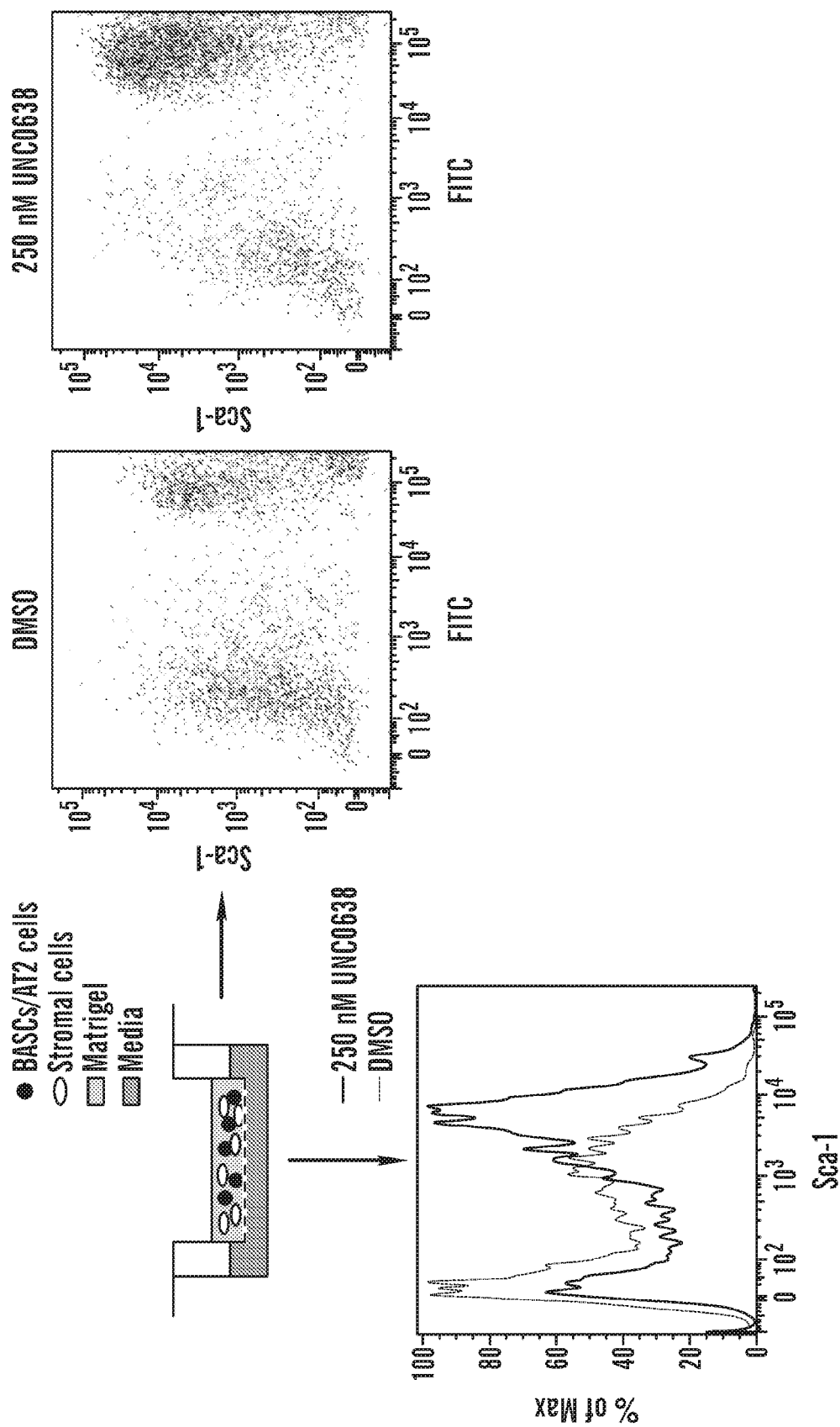
FIG. 2 depicts experimental schematics and FACS results demonstrating that G9a/G1p inhibition increases Sca-1 in BASC 3D co-culture.

The 3D cultures were resorted after 3 weeks growth with UNC0638 or a control and it was observed that the stem cell-derived cells (FITC high on the x axis of the FACs plots) had many more Sca-1 expressing cells (y axis on FACs plots) in UNC0638 vs DMSO control (DMSO is the solvent that UNC0638 is prepared in. Control wells have an equal amount of DMSO added to control for any effects addition of the solvent may have) (FIG. 2).

Figure 3:
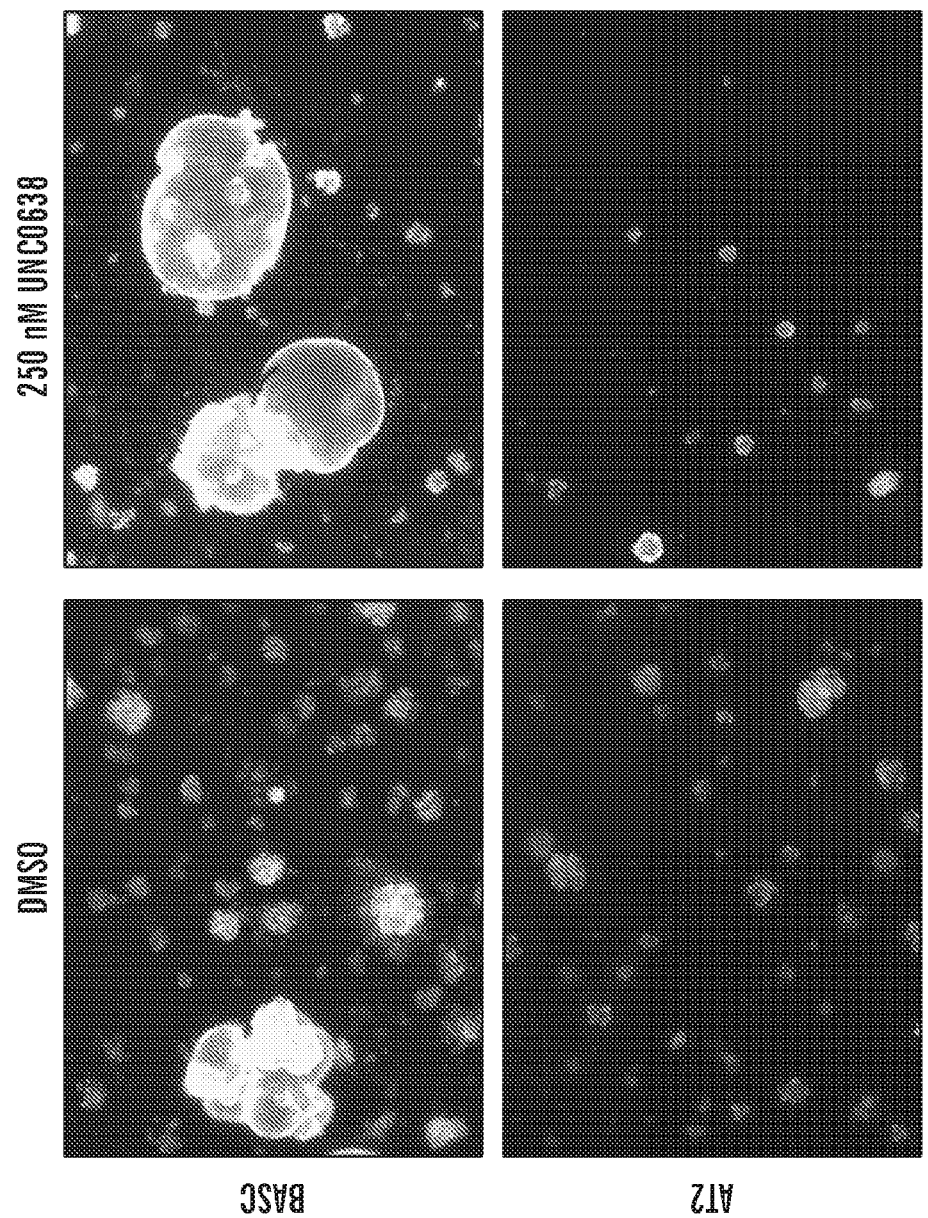
FIG. 3 depicts microscopy images demonstrating that G9a/G1p inhibition reduces alveolar organoid differentiation.

UNC0638 treated BASC (Bronchioalveolar Stem Cell) cultures have significantly fewer organoids with alveolar morphology and colonies with an undifferentiated phenotype (FIG. 3). UNC0638 treated AT2 (Alveolar Type 2) cultures have significantly fewer organoids. AT2 cells are only capable of producing alveolar morphological organoids (FIG. 3).

Figure 4:
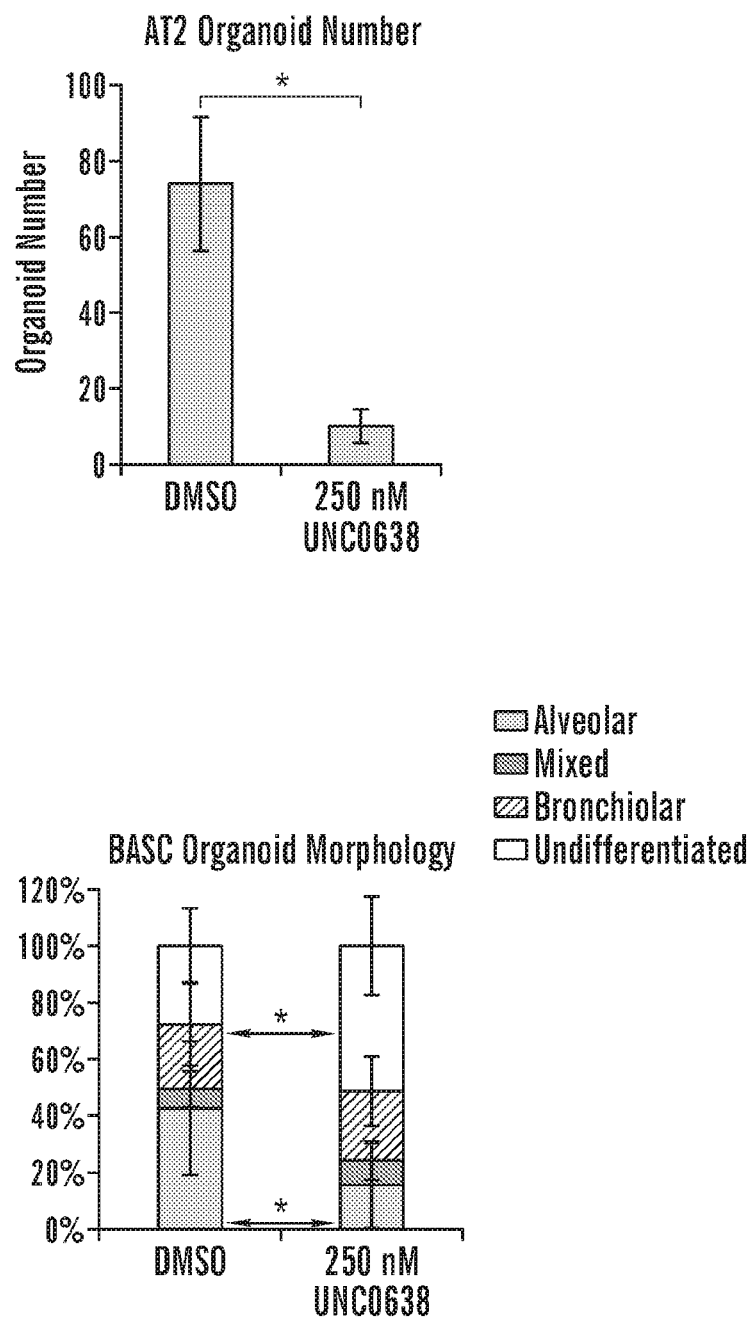
FIG. 4 depicts graphs demonstrating that G9a/G1p inhibition reduces alveolar organoid differentiation. Quantification and statistical analysis of organoid morphologies from cultures grown with UNC0638 or DMSO control. *=P<0.05, two tailed independent samples T-test
Figure 5:
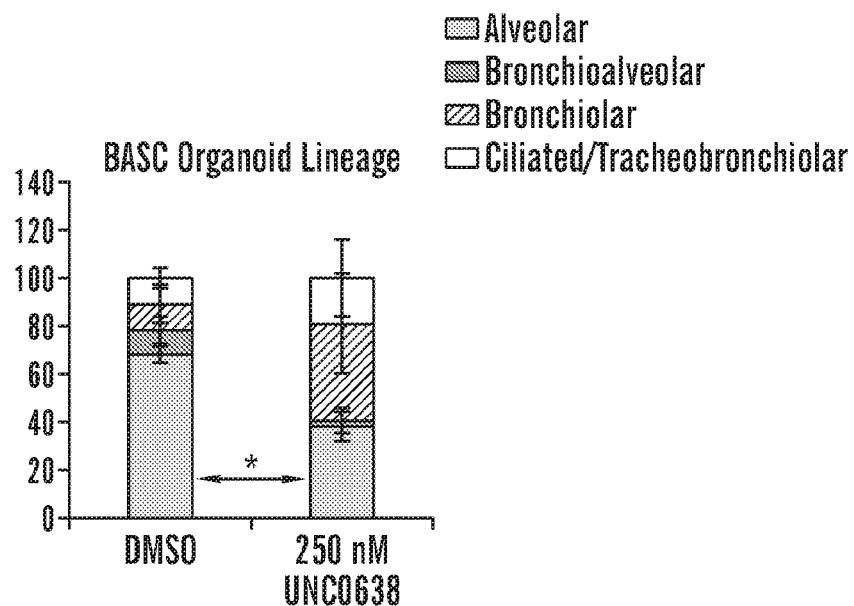
FIG. 5 depicts graphs demonstrating that G9a/G1p inhibition reduces alveolar organoid differentiation and increases ciliated organoid differentiation. Graphs depicts quantification of organoid lineage proportions in UNC0638 and DMSO treated cultures. On the top graph bronchiolar and tracheobronichiolar organoids are counted separately. On the bottom graph these organoids are counted together. *=P<0.05, two tailed independent samples T-test
Figure 5:
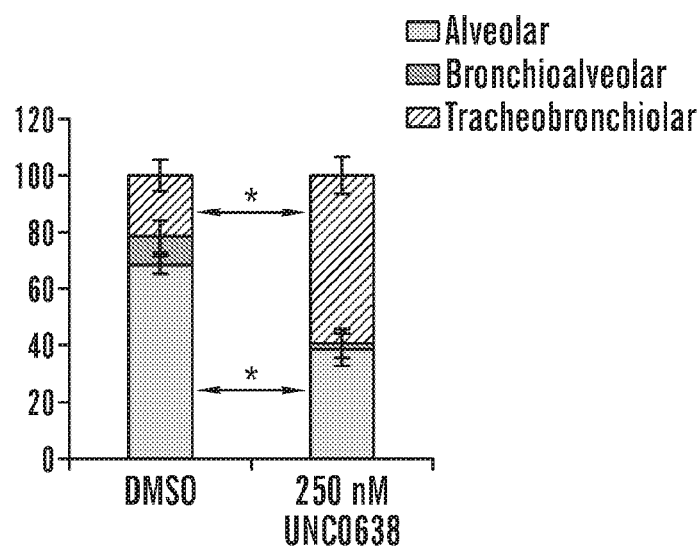

UNC0638 treatment significantly reduces organoid formation of Sca-1-ve sorted cells. UNC0638 treatment reduces the proportion of Sca-1+ve alveolar organoids and increases the proportion of small, undifferentiated organoids. (FIG. 4) 250 nM UNC0638 reduces alveolar colony formation and increase ciliated organoid formation (FIG. 5).

Organoids with visible movement are observed in control cultures, but are more frequent in 250 nM UNC0638 treated cultures. In UNC0638 treated cultures there were significantly more organoids that stained with Acetylated tubulin, a marker of Ciliated cells. H&E staining of these organoids reveals that many of the cells are muticiliated, like those of a trachea or large bronchiolar airway. Some organoids in UNC0638 cultures (and some rare organoids in DMSO cultures) can be seen to be visibly moving. They have currents in their lumen causing material within to move around. These currents are likely caused by beating cilia that line the inside of these organoids, just as beating ciliated cells line the inside of the upper lung airways. Currents are always counter clockwise, consistent with direction of cilia.

Figure 6:
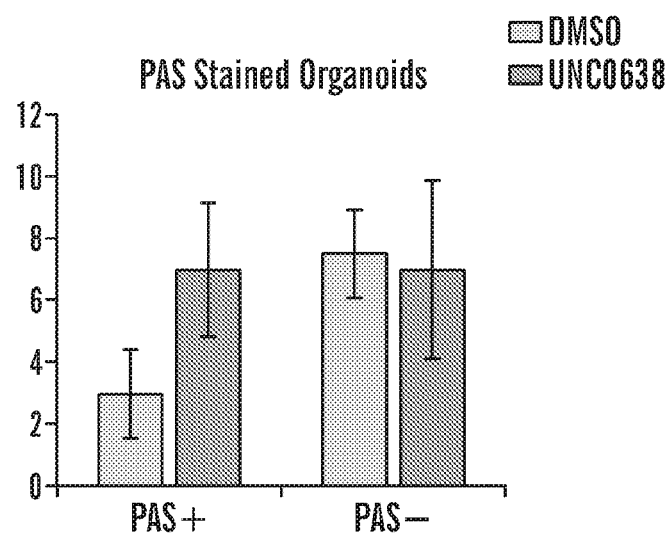
FIG. 6 depicts graphs of the quantification of PAS and Alcian Blue Stained Organoids in DMSO and UNC0638 treated Organoids.
Figure 6:
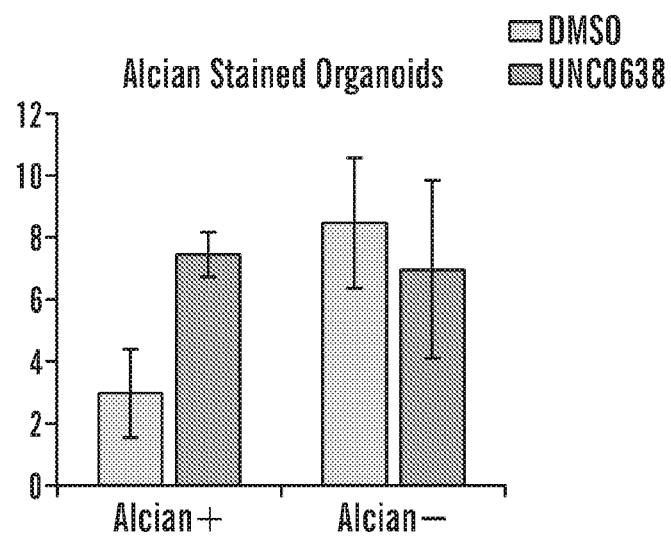

Ciliated organoids have large amounts of material that stain for PAS and Alcian Blue, like mucus produced by goblet cells in the lung upper airways. This material is likely what can be seen to revolve in the organoids with interior lumen currents. G9a/G1p inhibition increases the proportion and overall number of PAS/Alcian Blue Staining Organoids (FIG. 6). PAS stained cells resemble goblet cells that produce mucus in the upper airway. Immunofluoresence also shows these organoids have an outer layer of P63+ Keratin 5+ cells. This is precisely the same as the lung upper airways which have a lower layer of p63+ Keratin 5+ stem cells known as basal cells.

By treating lung stem cell cultures with UNC0638, an epigenetic inhibitor, the differentiation of lung stem cells can be directed to produce more organoids that resemble the large airways of the lung, with beating multiciliated cells, mucus-producing goblet like cells and P63+ Kertatin 5+ cells resembling basal stem cells. These organoids can be used to model respiratory diseases, the most obvious being cystic fibrosis which is caused by an inability of ciliated cells to clear mucus from the airways. The organoid culturers can be used as a platform to screen for drugs that effect the activity of these cell populations, or their rate of renewal.

What is claimed herein is:

1. A method comprising contacting lung stem and/or lung progenitor cells, in a three-dimensional (3D) culture and cocultured with endothelial cells, with an inhibitor of about 250 nM of H3K9me1/2 methyltransferase inhibitor UNC0638 or H3K9me1/2 methyltransferase inhibitor UNC0642 for at least three weeks, while the lung stem and/or lung progenitor cells are being cultured under conditions that support differentiation of lung stem and/or lung progenitor cells.

2. The method of claim 1, whereby the lung stem and/or lung progenitor cells differentiate to form mucus-producing goblet like cells.

3. The method of claim 1, whereby the lung stem and/or lung progenitor cells differentiate to form lung organoids comprising surfactant producing cells and mucus producing cells.

4. The method of claim 3, wherein the surfactant producing cells comprise at least one of secretory cells and club cells.

5. The method of claim 3, wherein the mucus producing cells comprise at least PAS+ cells, Alician Blue+ cells, Muc5AC+ cells and Goblet cells.

6. A method comprising contacting bronchioalveolar stem cells (BASCs), in a three-dimensional (3D) culture and cocultured with endothelial cells, with about 250 nM of H3K9me1/2 methyltransferase inhibitor UNC0638 or H3K9me1/2 methyltransferase inhibitor UNC0642, for at least three weeks, while the BASCs are being cultured under conditions that support differentiation of BASCs.

7. The method of claim 6, whereby the BASCs differentiate to form mucus-producing goblet like cells.

8. The method of claim 6, whereby the BASCs differentiate to form lung organoids comprising surfactant producing cells and mucus producing cells.

9. The method of claim 8, wherein the surfactant producing cells comprise at least one of secretory cells and club cells.

10. The method of claim 8, wherein the mucus producing cells comprise at least PAS+ cells, Alician Blue+ cells, Muc5AC+ cells and Goblet cells.

* * * * *